United States Patent [19]

White et al.

[11] Patent Number: 4,628,032

[45] Date of Patent: Dec. 9, 1986

[54] MONOCLONAL ANTIBODY SPECIFIC FOR A MAMMARY TUMOR CYTOPLASMIC ANTIGEN

[75] Inventors: Christine A. White, Encinitas; Renato Dulbecco, La Jolla; William R. Allen, Encinitas, all of Calif.

[73] Assignee: The Salk Institute for Biological Studies, San Diego, Calif.

[21] Appl. No.: 678,260

[22] Filed: Dec. 5, 1984

[51] Int. Cl.$^4$ .......................... C12N 5/00; C07K 15/00
[52] U.S. Cl. ...................................... 435/240; 435/68; 435/172.2; 435/7; 530/387; 935/104; 935/107; 935/110
[58] Field of Search ................ 435/7, 68, 70, 172.2, 435/240, 948, 935, 89, 90, 93, 95, 99, 100, 102–104, 107, 110; 260/112 R; 530/387

[56] References Cited

U.S. PATENT DOCUMENTS 4,172,124  10/1979  Koprowski et al. ................ 424/85
4,460,559  7/1984  Goldenberg ......................... 424/1.1

OTHER PUBLICATIONS

Dulbecco, R. et al., Proc. Natl. Acad. Sci., USA 80: 1033–1037 (2–1983).
Allen, R. et al., Proc. Natl. Acad. Sci., USA 81: 1203–1207 (2–1984).
Papsidero, L. D. et al., Cancer Research, vol. 43, pp. 1741–1747 (Apr. 1983).
Hand P. H. et al., Rational Basis for Chemotherapy, pp. 315–358, Alan R. Liss, Inc., N.Y., N.Y. (1983).
Nuti, M. et al., Int. J. Cancer, vol. 29(5), pp. 539–546 (1982), cited in Bio. Abstract 74084638.
Chee, D. O. et al., Cancer Research, vol. 42(8), pp. 3142–3147 (1982), cited in Bio. Abstract 75066138.
Natali, P. G. et al., Cancer Research, vol. 43(2), pp. 660–668 (1983), cited in Bio. Abstract 76011830.
Satwell, N. M. et al., Lab. Investig., vol. 51(2), pp. 225–232 (1984), cited in Bio. Abstract 79014680.
Press, M. F. et al., Lab. Investig., vol. 50(4), pp. 480–486 (1984), cited in Bio. Abstract 78050496.
Foster, C. S. et al., Hum. Pathol., vol. 15(6), pp. 502–513 (1984), cited in Bio. Abstract 78085252.
Ciocca, D. R. et al., Cancer Research, vol. 42(10), pp. 4256–4258 (1982), cited in Bio. Abstract 75073489.
Adams, D. J. et al., Cancer Research, vol. 43(9), pp. 4297–4301 (1983), cited in Chem. Abstract 99(19):154598g.
Ciocca, D. R. et al., J. Clin. Endocrinol Metab., vol. 57(3), pp. 496–499 (1983), cited in Bio. Abstract 77015383.
Adams, D. J. et al., Endocrinology, vol. 113(1), pp. 415–417 (1983), cited in Chem. Abstract 99(7):49819g.
White, C. A. et al., Cancer Research, vol. 45(3), pp. 1337–1343 (1985), cited in Bio. Abstract 79106323, not prior art.
Kufe, D. et al., Hybridoma, vol. 3(3), pp. 223–232 (1984), cited in Bio. Abstract 79060135.

Primary Examiner—Charles F. Warren
Assistant Examiner—M. Moskowitz
Attorney, Agent, or Firm—Fitch, Even, Tabin & Flannery

[57] ABSTRACT

An hybridoma cell line and the monoclonal antibody produced thereby are provided. The monoclonal antibody is specific for antigen found almost exclusively in the cytoplasm of human mammary tumor cells. The antibody is useful in diagnosing mammary tumors.

2 Claims, No Drawings

MONOCLONAL ANTIBODY SPECIFIC FOR A MAMMARY TUMOR CYTOPLASMIC ANTIGEN

The United States Government has certain rights in the invention disclosed herein as a result of support received under a grant from the National Cancer Institute.

The present invention is related to monoclonal antibodies and more particularly to monoclonal antibodies reactive with an antigen found in the cytoplasm of mammary tumor cells.

BACKGROUND OF THE INVENTION

Antibodies have long been used in medical diagnosis, e.g., determining blood types, and in biologioal experimentation. With development of techniques of producing monoclonal antibodies which make it possible to obtain homogenous, highly specific antibodies, Kohler G. and Milstein, C.: (1975) Nature (London) 256 495-497, the utility of antibodies has been greatly increased. Unlike antibody fraction which were previously available and which were actually heterogeneous mixtures of a number of antibody molecules reactive with a variety of antigenic determinants, the molecules in a monoclonal antibody are all identical and generally are reactive with a single antigenic determinant or a group of closely related antigenic determinants. Monoclonal antibodies are therefore much more precise probes for detecting the presence of a particular substance than were previous heterogeneous antibody fractions. The precise selectivity of monoclonal antibodies makes them particularly useful for diagnostic purposes and even as therapeutic agents against selected biological material, such as tumor cells. Monoclonal antibodies have been used to detect and isolate biological substances which were were previously unknown.

Generally, monoclonal antibodies are produced by immunizing an animal with a biological specimen or other foreign substance, obtaining antibody-producing cells from the animal, and fusing the antibody-producing cells with strains of neoplastic cells, e.g., tumor cells, to produce hybridomas which are isolated and cultured as monoclones. The monoclonal hybridomas may either be cultured in vitro or may be grown in vivo as tumors in a host animal. Because each antibody-producing cell produces a single unique antibody, the monoclonal cultures of hybridomas each produce a homogenous antibody fraction which may be obtained either from the culture medium of hybridoma cultures grown in vitro or from the ascitic fluid, or serum of a tumor-bearing host animal.

Not all of the hybridoma clones which result from fusing neoplastic cells with antibody-producing cells are specific for the desired foreign substance or antigen because many of the hybridomas will make antibodies which the animal's immune system has generated in reaction to other foreign substances. Even monoclonal antibodies against the subject antigen will differ from clone to clone because antibodies produced by different clones may react with different antigenic determinants of the same molecule. From each clone, therefore, it is necessary to obtain the resulting antibody or the antibody-containing medium, serum or ascitic fluid and test its reactivity with the subject biological material and to test its specificity by determining what other biological material, if any, it recognizes. While the necessity of characterizing the antibody of each clone adds to the complexity of producing monoclonal antibodies, the wide variety of homogeneous antibodies which may be obtained gives investigators a number of very precise tools to map the structure and development of somatic cells.

SUMMARY OF THE INVENTION

A monoclonal antibody is produced which is specific for antigens found predominantly in human mammary tumor cells. Mice are inoculated with human mammary tumor cells, and spleen cells or lymph node cells are obtained from the inoculated mice and fused with mouse tumor cells. Monocultures of the fused cells are produced, and the antibodies obtained from the monoclones are tested for their ability to react with a variety of randomly obtained human mammary tumor tissues. In order to select a monoculture which produces an antibody with the desired characteristics, the reactivity of the antibody with other cells, including both normal human cells and other human tumor cells is investigated. A monoclonal antibody from one hybridoma clone is reactive with a cytoplasmic antigen found almost exclusively in mammary tumor cells. The monoclonal antibody is particularly useful for diagnosing mammary tumors.

DETAILED DESCRIPTION OF THE PREFERRED EMBODIMENTS

Human mammary carcinoma currently represents the leading cause of cancer death in women in the United States with more than 150,000 new cases diagnosed each year. The histopathologioal classification of human mammary carcinomas is currently dependent on morphologic description alone. Approximately 80% are infiltrating ductal carcinomas, 10% are infiltrating lobular carcinomas, and the remaining 10% comprise a number of histologic types including intraductal carcinoma. Excepting inflammatory carcinoma, for the most part, morphology has not proven to be a good predictor of clinical prognosis or response to therapy. Indeed, extent of disease (tumor size and nodal positivity) have continued to determine clinical management. Recently, with the advent of estrogen and progesterone receptor determinations, correlations have begun to be made between clinical variables and biologic characteristics of malignant mammary cells.

In accordance with the invention, a hybridoma is developed which produces a monoclonal antibody which is generally reactive with human mammary carcinomas, specifically reacting with a cell cytoplasmic antigen found almost exclusively in mammary tumor cells. The monoclonal antibody is most strongly reactive with breast carcinomas of poorly differentiated and infiltrating ductal morphology, irrespective of estrogen or progesterone receptor status. The antibody is less strongly reactive with papillary, comedo, and intraductal carcinomas. It does not seem to differentiate primary from metastatic breast cancer. It does not bind to normal human breast luminal or myoepithelial cells, nor with benign mammary tumors. It reacts with some cases of mammary fibrocystic disease. As the antibody detects an antigen found almost exclusively in human mammary carcinomas, it is useful in diagnosing mammary carcinomas and for distinguishing mammary carcinomas from nonmammary carcinomas.

A monoclonal antibody to the breast carcinoma cell line MCF-7 was produced utilizing the technique of Kohler and Milstein supra. The mammary tumor cell line MCF-7 (Soule, H.D., et al. JNCI, 51:1409–1413 (1973)), was cultured in DMEM with 10% fetal calf serum and NEAA (8.9 mg/L L-alanine, 15.0 mg/L L-asparagine, 13.3 mg/L L-aspartic acid, 14.7 mg/L L-glutamic acid, 7.5 mg/L L-glycine, 11.5 mg/L L-proline, 10.5 mg/L L-serine).

BALB/c mice were immunized with $10^6$ MCF-7 cells injected intraperitoneally every 3 weeks for a total of 3 to 4 injections. The mice were sacrificed three days after the last injection and their spleens were taken. A spleen cell suspension was prepared, and the resulting cell suspension was washed by two centrifugations (800×g) in protein-free Dulbecco's modified Eagles medium.

Because the antibody-producing cells obtained from the spleen do not independently reproduce, and thus cannot be cultured, they are fused with cells which may be independently cultured either in vivo or in vitro so that the genetic and metabolic processes of the fused hybridomas have characteristics of each of the parent cells, and it is intended that certain of the cells obtained will have the capability to independently reproduce and to produce the antibody of the antibody-producing parent cell. Some tumor cells, particularly myeloma cells, may be advantageously fused with antibody-producing cells to produce hybridomas. Although it is not necessary, it is preferred that the tumor cells and antibody-producing cells be derived from the same species to enhance the likelihood that the genetic and biochemical properties of the parent cells will be compatible and thus produce viable and stable hybridomas. A number of myeloma cultures have been characterized, and herein, mouse-derived, nonantibody-producing myeloma cell line, PAI obtained from Dr. Theo Stachlin, Basil, Switzerland, J. Stocker, *Research Disclosure* 21713, 155–157 (1982), were used to produce the hybridomas. It is to be understood that other tumor lines, which include but are not limited to P3NS1, Y3, SP2/0 and their derivatives, may also be used.

It is advantageous to select a myeloma line which does not produce antibody so that the resulting hybridoma will only produce the antibody of the parent spleen or lymph node cell. This is particularly important if the antibody might be used internally where it is undesirable to introduce extraneous antibodies which could produce side reactions.

The myeloma cells are maintained in Dulbecco's modified Eagle's medium supplemented with 10% horse serum. $10^7$ myeloma cells and $10^8$ cells obtained from the immunized mice are resuspended for fusion in a 45% solution (v/v) of polyethelyene glycol 1500. Cell hybrids are selected in hypoxanthine aminopterin thymidine (HAT) medium all growth in HAT medium being indicative of successful hybridization of mouse spleen and mouse myeloma cells.

Clones of hybridomas may be grown in vitro according to known tissue culture techniques such as is described by Cotten et al., *Eur. J. Immunol.* 3, 136 (1973). Alternatively, hybridomas may be grown in vivo as tumors in a histocompatible animal or in athymic nude mice. The antibodies may be recovered from the in vitro culture medium (the supernatant of the clone) or from the serum or ascitic fluid of the animal by means known in the art, e.g., Gerhard et al., *Proc. Natl. Acad. Sci.*, 75, 1510–1514 (1978). In some cases it may be advantageous to obtain the antibodies directly from the cells of the culture or tumor.

The initial specificity screening of hybridoma supernatants using live, dried and lysed MCF-7, MDA-157, DU4475 (other mammary carcinoma cell lines which were cultured in the manner that MCF-7 was cultured) and a human foreskin fibroblast (HFF) cell line as target cells was performed by ELISA assay. Hybridomas producing supernatant reactive with the cytosol of the tumor cell lines, or with the dried or live tumor cells and entirely unreactive with HFF cell material were selected as potential producers of antibody specifically reactive with a mammary tumor cell cytoplasmic antigen.

Selected hybridomas were cultured in DMEM supplemented with 10% horse serum, NEAA, $10^{-5}$M mercaptoethanol.

When a useful hybridoma clone is produced it is generally advantageous to reclone the cell line to avoid overgrowth of cultures with variant cells no longer producing antibody. Because the hybridoma contains some, but not all, of the genetic material of each parent cell, the full characteristics of the hybridoma are not known. Often a hybridoma clone, due to original genetic deficiency or subsequent chromosome loss, after several passages may lose its ability to reproduce and/or to produce the particular antibody. Accordingly, it is important, soon after the initial hybridization, that a hybridoma clone of interest is recloned to insure the availability of functioning strains of the antibody-producing hybridoma. By recloning is meant to isolate individual cells and expand them into cultures which are clones.

A hybridoma cell line culture initially designated as 3B18 and its reclones produce a monoclonal antibody specific for a cytoplasmic antigen that occurs almost exclusively in human mammary carcinoma cells. The 3B18 cell line is on deposit at the American Tissue Culture Collection of 12301 Parklawn Dr., Rockville, Md. 20852 and has been assigned the accession number HB-8654.

In immunoperoxidase assays, 3B18 reacted with cytoplasm of 25 of 29 specimens or about 85% of human mammary carcinoma, but not normal mammary epithelium or benign mammary epithelial hyperplasia. Because the mammary carcinoma tissues Were randomly obtained, the antibody is expected to react With about the same proportion of other randomly obtained human mammary carcinoma tissues. It reacted with a variable fraction of the cells in some cases of mammary fibrocystic disease. The antibody reacts most strongly with poorly differentiated infiltrating ductal breast cancers. It did not react with any normal human tissues, breast epithelium nor any other normal cells of the adult human body. It reacts with about 10% of cancers of epithelial origin other than breast cancer.

The isotype of monoclonal antibody 3B18 was determined by Ouchterlony gel immunodiffusion with rabbit antiserum to mouse IgG1, IgG2a, IgG2b, IgG3, IgM and IgA (Miles Laboratory). 3B18 monoclonal antibody was determined to be of the IgGI isotype.

Portions of fresh normal and malignant tissues were obtained from the Surgical and Anatomical Pathology Departments of the UCSD Hospital and the Veterans Hospital, San Diego. Fresh frozen tissues were obtained from the biological carcinogenesis branch of the National Cancer Institute. The reactivity of the 3B18 monoclonal antibody with the several tissues was determined by immunoperoxidase staining.

Tissues were coated with Tissue Tek OCT Compound (Scientific Products) and frozen at −70° C. Sections of frozen tissue blooks 4 μM thick were cut on the microtome/cryostat, mounted on glass slides and stored at −70° C. Mounted slides were stained by an indirect immunoperoxidase assay.

Briefly, slides were hydrated with PBS, then partially air-dried. The monoclonal antibody was overlayed onto sections and incubated at room temperature for 30 minutes in a humid chamber. Sections were then overlaid with a 1:100 dilution of horseradish peroxidase conjugated with goat anti-mouse immunoglobulin and incubated for 30 minutes. The color reaction was developed with diaminobenzidine (0.6 mg/ml) and 0.03% hydrogen peroxide. Cells were counterstained in hematolxylin, washed in water, dehydrated in 100% ethyl alcohol, cleared in xylene, mounted in Permount, covered with a coverslip and examined using a Zeiss microscope. The reactivities of 3B18 with human mammary carcinoma cell lines and other tumor tissues are shown in Table 1.

TABLE 1

BINDING OF 3B18 ANTIBODY TO HUMAN MAMMARY CARCINOMA CELL LINES AND OTHER HUMAN TUMOR TISSUES

| | 3B18 |
|---|---|
| CELL LINES (live) | |
| *Mammary carcinoma* | |
| MCF-7 | − |
| MDA-157 | − |
| DU4475 | − |
| *Non-mammary* | |
| HFF | − |
| PA1 | − |
| TISSUES (frozen) | |
| Human mammary carcinoma (total) | +(25/29) |
| Primary infiltrating ductal carcinoma | +(16/17) |
| Infiltrating ductal cancer metastatic to liver, lung omentum and brain | +(5/5) |
| Intraductal, papillary, colloid mammary carcinomas | +(3/6) |
| Comedo carcinoma | +(1/1)* |
| Cystosarcoma phylloides | −(1) |
| Papillary ductular hyperplasia, sclerosing adenosis | −(2/2) |
| Fibrocystic disease | +(2/2) (isolated cells) |
| Fibroadenoma | +(1/1) |
| Normal mammary epithelium | −(4/4) |

+ = positive immunoperoxidase reaction (usually strong)
− = no reaction
*weak reaction Table 1 shows that the antibody did react with some cases of mammary fibrocystic disease and with one of two colon carcinomas tested. 3B18 stained papillary, comedo, and intraductal types of breast cancer less strongly than it did specimens of infiltrating ductal or poorly differentiated breast carcinomas.

Table 2 below summarizes the reactivities of 3B18 with normal tissues and nonmammary malignancies. 3B18 had no reactivity with any of the 28 normal and 17 of 18 malignant tissues tested.

TABLE 2

BINDING OF ANTIBODY 3B18 TO NORMAL TISSUES AND NONMAMMARY MALIGNANCIES

| | 3B18 |
|---|---|
| NORMAL TISSUES | |
| Epidermis | − |
| Salivary gland | − |
| Thyroid | − |
| Adrenal | − |
| Lung | − |
| Bronchus | − |
| Heart | − |
| Aorta | − |
| Esophagus | − |
| Stomach | − |
| Small bowel | − |
| Large bowel | − |
| Liver (2) | − |
| Pancreas | − |
| Gall bladder | − |
| Spleen | − |
| Lymph nodes | − |
| Kidney (2) | − |
| Bladder | − |
| Ovary | − |
| Testis | − |
| Cervix | − |
| Uterus | − |
| Bone marrow | − |
| Brain | − |
| NONMAMMARY MALIGNANCIES | |
| *Lung* | |
| Squamous cell cancer | − |
| Adenocarcinoma | − |
| Small cell cancer | |
| *Gastrointestinal* | |
| Gastric cancer | − |
| Cholangiocarcinoma | − |
| Pancreatic cancer | − |
| Colon cancer (2) | −/+ |
| *Genito-urinary* | |
| Cervix cancer | − |
| Ovarian cancer | − |
| Bladder cancer | − |
| Renal cancer | − |
| Prostate cancer (2) | − |
| *Lymphoma* | |
| T cell | − |
| Mesothelioma | − |
| Melanoma | − |

Because 3B18 antibody detects antigens found almost exclusively in human mammary carcinomas, this antibody is presently useful for diagnosing mammary carcinoma cells and for ascertaining the mammary tumor origin of a tumor that has metastasized.

Modifications obvious to one with ordinary skill in the art may be made without departing from the scope of the present invention. For example, antibody production may be induced in the host animal by inoculating the animal with cell mammary cell cytoplasm rather than with complete mammary tumor cells.

Various features of the invention are set forth in the following claims.

What is claimed is:

1. A cell line selected from the group consisting of hybridoma cell line 3B18 and antibody-producing reclones thereof.

2. A monoclonal antibody obtained from a culture of a cell line selected from the group consisting of hybridoma cell line 3B18 and antibody-producing reclones thereof.

* * * * *